(12) United States Patent
Celi et al.

(10) Patent No.: US 10,517,316 B2
(45) Date of Patent: *Dec. 31, 2019

(54) COMBINATION OF 25-HYDROXYVITAMIN D AND ANTIOXIDANTS/ANTI-INFLAMMATORIES FOR BOVINE HEALTH

(71) Applicant: DSM IP ASSETS B.V., Heerlen (NL)

(72) Inventors: Pietro Celi, Kaiseraugst (CH); Shuen Ei Chen, Kaiseraugst (CH); Thau Kiong Chung, Kaiseraugst (CH)

(73) Assignee: DSM IP ASSETS B.V., Heerlen (NL)

(*) Notice: Subject to any disclaimer, the term of this patent is extended or adjusted under 35 U.S.C. 154(b) by 0 days.

This patent is subject to a terminal disclaimer.

(21) Appl. No.: 15/542,187

(22) PCT Filed: Jan. 15, 2016

(86) PCT No.: PCT/EP2016/050764
§ 371 (c)(1),
(2) Date: Jul. 7, 2017

(87) PCT Pub. No.: WO2016/113389
PCT Pub. Date: Jul. 21, 2016

(65) Prior Publication Data
US 2018/0264010 A1 Sep. 20, 2018

Related U.S. Application Data

(60) Provisional application No. 62/103,769, filed on Jan. 15, 2015.

(30) Foreign Application Priority Data

May 8, 2015 (EP) .................................. 15166937

(51) Int. Cl.
| | |
|---|---|
| A23K 20/174 | (2016.01) |
| A23K 20/179 | (2016.01) |
| A23K 50/10 | (2016.01) |
| A23K 50/75 | (2016.01) |
| A61K 9/00 | (2006.01) |
| A61K 31/122 | (2006.01) |
| A61K 31/197 | (2006.01) |
| A61K 31/355 | (2006.01) |
| A61K 31/375 | (2006.01) |
| A61K 31/4188 | (2006.01) |
| A61K 31/455 | (2006.01) |
| A61K 31/519 | (2006.01) |
| A61K 31/525 | (2006.01) |
| A61K 31/593 | (2006.01) |
| A61K 31/675 | (2006.01) |
| A61K 33/04 | (2006.01) |
| A61K 33/26 | (2006.01) |

(Continued)

(52) U.S. Cl.
CPC .......... *A23K 20/174* (2016.05); *A23K 20/179* (2016.05); *A23K 20/30* (2016.05); *A23K 50/10* (2016.05); *A23K 50/42* (2016.05); *A23K 50/48* (2016.05); *A23K 50/75* (2016.05); *A61K 9/0056* (2013.01); *A61K 31/015* (2013.01); *A61K 31/122* (2013.01); *A61K 31/197* (2013.01); *A61K 31/355* (2013.01); *A61K 31/375* (2013.01); *A61K 31/4188* (2013.01); *A61K 31/455* (2013.01); *A61K 31/519* (2013.01); *A61K 31/525* (2013.01); *A61K 31/593* (2013.01); *A61K 31/675* (2013.01); *A61K 33/04* (2013.01); *A61K 33/26* (2013.01); *A61K 33/32* (2013.01); *A61K 33/34* (2013.01); *A61P 3/06* (2018.01); *A61P 3/08* (2018.01); *A61P 9/00* (2018.01); *A61P 15/00* (2018.01); *A61P 15/08* (2018.01); *A61P 39/00* (2018.01)

(58) Field of Classification Search
None
See application file for complete search history.

(56) References Cited

U.S. PATENT DOCUMENTS

| | | | |
|---|---|---|---|
| 6,034,075 A | 3/2000 | Thys-Jacobs | |
| 7,632,518 B2 * | 12/2009 | Tritsch | A23D 7/0053 424/439 |

(Continued)

FOREIGN PATENT DOCUMENTS

| | | |
|---|---|---|
| JP | H11-35469 | 2/1999 |
| JP | 2005-519894 | 7/2005 |

(Continued)

OTHER PUBLICATIONS

Stankiewicz, T.; Blaszczyk, B. Macro-elements compsoition of cystic and follicular fluid in the ovaries and their relationship to peripheral blood concentration in sows. Acta Veterinaria-Beograd, 65(2), 217-225. (Year: 2015).*

(Continued)

*Primary Examiner* — Jessica Worsham
(74) *Attorney, Agent, or Firm* — Nixon & Vanderhye P.C.

(57) ABSTRACT

This invention relates to the use of the combination of 25-hydroxyvitamin D3 ("25-OH D3") and antioxidants/anti-inflammatories (ascorbic acid, vitamin E and at least one carotenoid) to make a pharmaceutical, nutraceutical or food supplement which can ameliorate various problems observed in bovines connected cystic ovarian disease, or increasing 17-β estradiol levels. Feed and premixes containing the 25-OH D3 and antioxidants/anti-inflammatories and premixes are also provided.

3 Claims, 7 Drawing Sheets

(51) Int. Cl.
A61K 33/32 (2006.01)
A61K 33/34 (2006.01)
A23K 50/42 (2016.01)
A23K 50/48 (2016.01)
A61P 3/08 (2006.01)
A61P 39/00 (2006.01)
A61P 9/00 (2006.01)
A61P 3/06 (2006.01)
A61K 31/015 (2006.01)
A23K 20/20 (2016.01)
A61P 15/00 (2006.01)
A61P 15/08 (2006.01)

(56) References Cited

U.S. PATENT DOCUMENTS

2003/0125229 A1 7/2003 Rodriguez
2006/0034912 A1 2/2006 Giordano et al.
2006/0069151 A1 3/2006 Barella et al.
2010/0098779 A1 4/2010 Balzer et al.
2010/0112162 A1 5/2010 Tritsch et al.
2013/0011377 A1 1/2013 Perrin et al.
2013/0281533 A1 10/2013 Yamka et al.

FOREIGN PATENT DOCUMENTS

JP 2006-510647 3/2006
JP 2011-511826 4/2011
JP 2011-511827 4/2011
JP 2012-509253 4/2012
SU 1748784 7/1992
WO WO 2008/031602 3/2008
WO WO 2010/057811 5/2010
WO WO 2014/191153 12/2014
WO WO 2014/202433 12/2014

OTHER PUBLICATIONS https://www.merriam-webster.com/medical/supraphysiological retrieved on May 8, 2019.*
International Search Report for PCT/EP2016/050764 dated Apr. 19, 2016, 3 pages.
Written Opinion of the ISA for PCT/EP2016/050764 dated Apr. 19, 2016, 8 pages.
[Online] About DSM: "DSM Vitamin Supplementation Guidelines 2011 Heath @Bullet Nutrition @Bullet Materials for domestic animals Guidelines for Optimum Vitamin Nutrition DSM vitamin supplementation guidelines are designed to provide typical industry practices. Optimum Vitamin Nutrition co", Aug. 11, 2014, pp. 2-3.
Walzem et al., "Obesity-Induced Dysfunctions in Female Reproduction: Lessons from Birds and Mammals", Advances in Nutrition: An International Review Journal, vol. 5, No. 2, Mar. 1, 2014, pp. 199-206.
Muscogiuri et al., "Low Levels of 25(OH) D and insulin-resistance: 2 unrelated features or a cause-effect in PCOS?" Clinical Nutrition, vol. 31, No. 4, pp. 476-480.
Amengual et al., "Beta-Carotene Reduces Body Adiposity of Mice via BCMO1", PLoS ONE, vol. 6, No. 6, Jun. 1, 2011, 14 pages.
Bhuvaneswari et al., "Astaxanthin restricts weight gain, promotes insulin sensitivity and curtails fatty liver disease in mice fed an obesity-promoting diet", Process Biochemistry, vol. 45, No. 8, Aug. 1, 2010, pp. 1406-1414.
Buryakov et al., "Feeding of broiler chicks—involves addn. of sodium ascorbate to basic feed mix to increase live wt. gain", WPI / THOMSON, vol. 1993, No. 27, Jul. 23, 1992.
Ruschkowski et al., Ionic and Endocrine Characteristics of Reproductive Failure in Calcium-Deficient and Vitamin D-Deficient Laying Hens, Poultry Science, vol. 71, Issue 10, pp. 1722-1732.
Vanga et al., "Role of Vitamin D in Cardiovascular Health", The American Journal of Cardiology, 2010, pp. 788-805.
Villar-Patiño et al., "Effects of Dietary Supplementation with Vitamin C or Vitamin E on Cardiac Lipid Peroxidation and Growth Performance in Broilers at Risk of Developing Ascites Syndrome", American Journal of Veterinary Research, American Veterinary Medicine Association, vol. 63, No. 5, May 1, 2002, pp. 673-676.
International Search Report for PCT/EP2016/050749 dated May 23, 2016, 3 pages.
International Search Report for PCT/EP2016/050751 dated Apr. 26, 2016, 3 pages.
International Search Report for PCT/EP2016/050753 dated Apr. 20, 2016, 3 pages.
International Search Report for PCT/EP2016/050755 dated Apr. 21, 2016, 3 pages.
International Search Report for PCT/EP2016/050759 dated Apr. 26, 2016, 4 pages.
International Search Report for PCT/EP2016/050762 dated Apr. 29, 2016, 5 pages.
Office action for U.S. Appl. No. 15/541,852 dated May 30, 2018 (12 pages).
Office action for U.S. Appl. No. 15/542,091 dated Aug. 10, 2018 (17 pages).
Office action for U.S. Appl. No. 15/542,143 dated Aug. 10, 2018 (14 pages).
Office action for U.S. Appl. No. 15/542,500 dated Sep. 10, 2018 (16 pages).
Office action for U.S. Appl. No. 15/542,509 dated Sep. 7, 2018 (16 pages).
Official Action, Colombia Appln. No. NC2017/0007058, Aug. 17, 2018 (English Translation).
Written Opinion of the ISA for PCT/EP2016/050749 dated May 23, 2016, 8 pages.
Written Opinion of the ISA for PCT/EP2016/050751 dated Apr. 26, 2016, 6 pages.
Written Opinion of the ISA for PCT/EP2016/050753 dated Apr. 20, 2016, 6 pages.
Written Opinion of the ISA for PCT/EP2016/050755 dated Apr. 21, 2016, 8 pages.
Written Opinion of the ISA for PCT/EP2016/050759 dated Apr. 26, 26 Apr. 2016, 8 pages.
Written Opinion of the ISA for PCT/EP2016/050762 dated Apr. 29, 2016, 7 pages.
Franks, S. "Polycystic Ovary Syndrome" NEJM, 333 (13), 853-861 (Year: 1995).
Franks, S. "Adult polycystic ovary syndrome begins in childhood" Best Practice & Research Clinical Endocrinology and Metabolism, 16 (2), 263-272 (Year: 2002).
Garcia et al., "Use of Vitamin $D_3$ and Its Metabolites in Broiler Chicken Feed on Performance, Bone Parameters and Meat Quality" Asian-Aust. J. Anim. Sci, vol. 26, No. 3: 408-415 (Mar. 2013).
Nutrient Requirements of Poultry: Ninth Revised Edition, The National Academics of Sciences Engineering Medicine, 176 pages (1994).
Rosenfield, R.L. et al. "Dysregulation of cytochrome P450c17α as the cause of polycystic ovarian syndrome" Fertility and Sterility 1990, 53 (5), 785-791 (Year: 1990).
Office Action issued in U.S. Appl. No. 15/541,793 dated Mar. 25, 2019.
Office Action issued in U.S. Appl. No. 15/541,852 dated Dec. 27, 2018.
Office Action issued in U.S. Appl. No. 15/542,091 dated May 23, 2019.
Office Action issued in U.S. Appl. No. 15/542,143 dated Mar. 8, 2019.
Office Action issued in U.S. Appl. No. 15/542,500 dated May 23, 2019.
Office Action issued in U.S. Appl. No. 15/542,509 dated May 23, 2019.
Office Action issued in JP Appln. No. 2017-534244 dated Jul. 23, 2019 (w/ translation).
Office Action issued in U.S. Appl. No. 15/541,793 dated Sep. 17, 2019.

(56) References Cited

OTHER PUBLICATIONS

Office Action issued in JP Appln. No. P2017-530279 dated Sep. 3, 2019 (translation).

* cited by examiner

FIGURE 1, ctd.
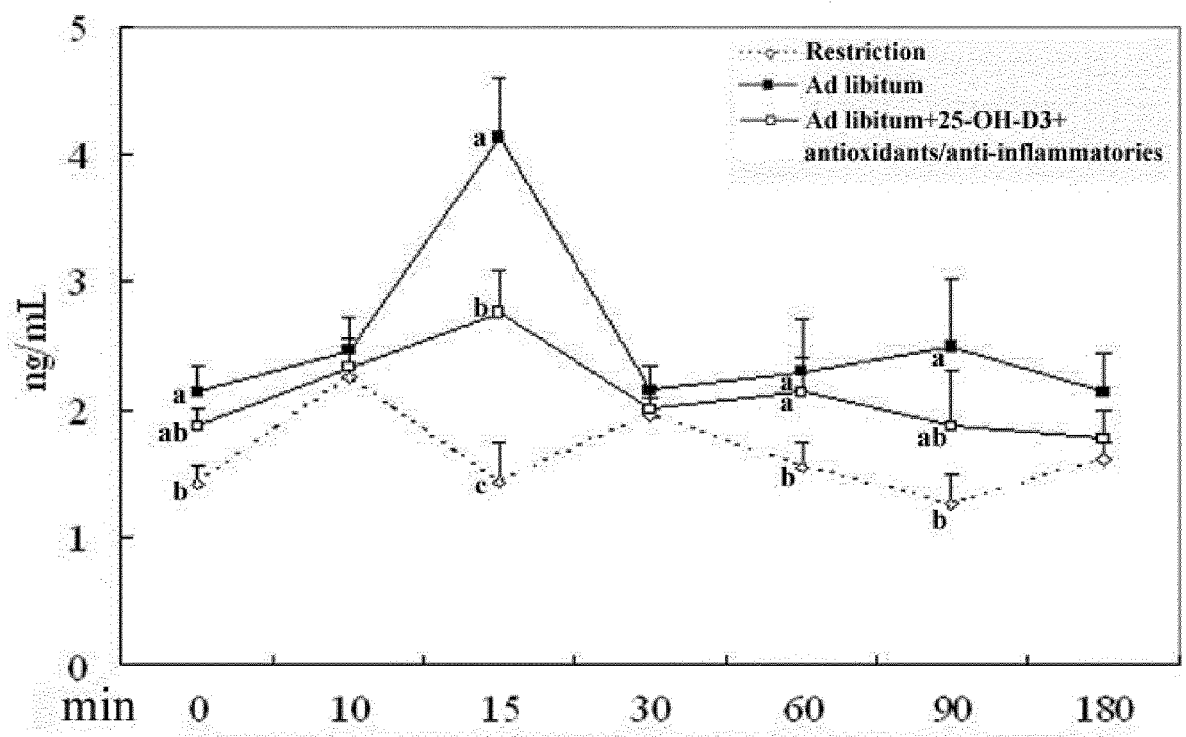

FIGURE 2, ctd.
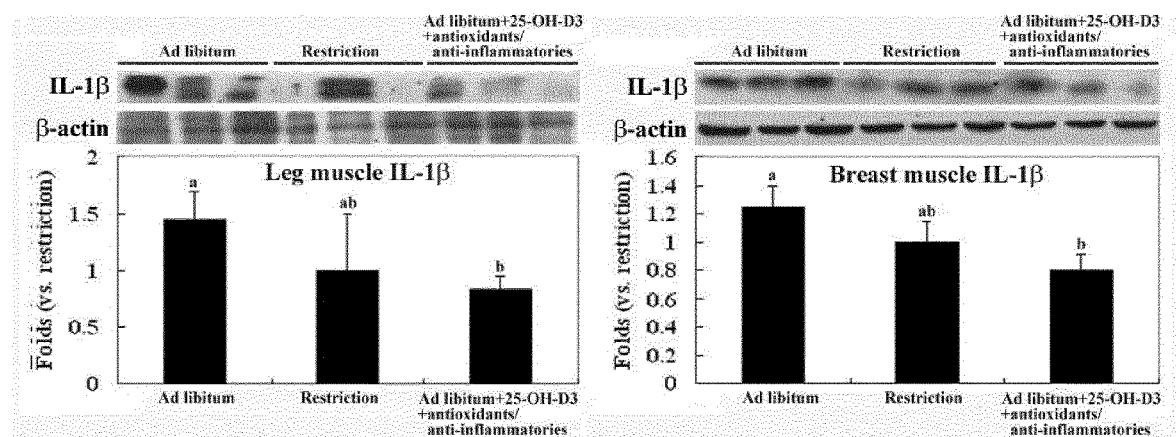

FIGURE 2, ctd.
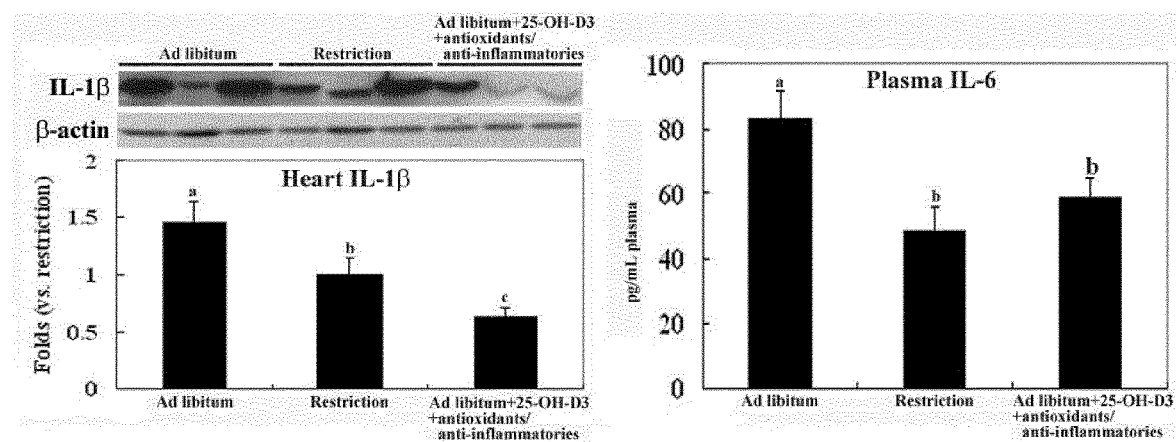

COMBINATION OF 25-HYDROXYVITAMIN D AND ANTIOXIDANTS/ANTI-INFLAMMATORIES FOR BOVINE HEALTH

This application is the U.S. national phase of International Application No. PCT/EP2016/050764 filed Jan. 15, 2016 which designated the U.S. and claims the benefit of U.S. Provisional Application No. 62/103,769 filed Jan. 15, 2015 and claims priority to EP Patent Application No. 15166937.1 filed May 8, 2015, the entire contents of each of which are hereby incorporated herein by reference.

BRIEF DESCRIPTION OF THE INVENTION

This invention relates to the combination of 25-hydroxyvitamin D ("25-OH D3" and/or "25-OH D2") and antioxidants/anti-inflammatories (ascorbic acid, Vitamin E and a carotenoid) for use in bovine feed. This combination of nutritional supplements can contribute to ovarian health and healthy circulating 17-β estradiol levels, thus prolonging the productive life of milking cows.

BACKGROUND OF THE INVENTION

One animal model for ovarian disease is poultry. The domestic laying hen can develop ovarian cancer with a high prevalence. See Johnson et al 2013 *Nature* 13: 432-436, and Walzem et al 2014 *Advances in Nutrition* 5: 199-206. The progression of hen ovarian cancer as well as locations of metastatic growths and ascites are similar to that observed in women.

Some breeds of poultry experience hyperphagia-related obesity. Generally, the farmer will restrict the amount of food offered to the flock to prevent the adverse consequences of obesity. However, it is often difficult to determine the proper amount of feed to provide which will ensure the desired growth of the flock, and under restricted feeding conditions, individuals can become aggressive and not only injure other birds, but become obese themselves.

Female broiler breeders overfed during reproductive development not only produce excess large yellow ovarian follicles but also generate a greater number of atretic yellow follicles and commonly display erratic oviposition and defective egg syndrome (EODES) that include several reproductive problems such as follicular atresia, the production of soft-shelled or membranous eggs, double-yolked eggs, egg yolk peritonitis (presence of egg yolk in the abdominal cavity), multiple egg days and oviposition not occurring in sequence, resulting in increased production of unsettable eggs.

Controlled studies reported that voluntary feeding (i.e., broiler breeder hens fed to satiation) resulted in poor egg production, high rate of mortality and abnormal ovarian structure (mainly overt hierarchical follicle atresia). In contrast to feed-restricted hens, voluntary feeding also induced metabolic dysregulations that comprised enhanced adiposity; hepatic triacylglycerol accumulation; and elevated concentrations of plasma glucose, non-esterified fatty acids, very low density lipoprotein, triacylglycerol, phospholipids, ceramide and sphingomyelin.

Furthermore, hepatic and circulating ceramide and sphingomyelin accumulation, and up-regulation of proinflammatory IL-1β expression in liver and adipose tissues systemically manifested the development of lipotoxicity in feed-satiated hens. Ceramide is a key intermediate linking certain nutrients (i.e. saturated fats) and inflammatory cytokines (e.g. tumor necrosis factor-α, TNFα) to the regulation of cell function and antagonizing insulin signaling and mitochondrial function. Moreover, as a result of its toxic effects on particularly susceptible cell types, ceramide has the capacity to damage the heart, pancreas, and vasculature. Lipotoxicity leading to impaired ovarian dysfunctions, including follicle atresia, ovarian regression, and a decline of circulating estradiol levels in feed-satiated hens, was further exemplified by ceramide accumulation and up-regulation of IL-1β, serine palmitoyltransferase, and sphingomyelinase transcript abundance, but suppressed protein kinase Akt activation within the hierarchical follicles. In vivo evidence has thus delineated the actions of ceramide and IL-1β in mediating overfeeding-induced follicle atresia and progression of ovarian involution in broiler hens.

Despite restricted feeding regimen strictly implemented in commercial broiler breeder flocks, it is still very easy to overfeed breeder hens due to their intrinsic hyperphagia. Furthermore, breeder farm managers are confronted as to when and how to feed before and during the start of egg production as well as towards, during and after peak production. The basic fundamental question to ask what and how management and nutritional tools breeder farm managers can apply and implement to ameliorate the adverse and deleterious effects of reproductive efficiency associated with obesity in overweight hens.

Hy•D® (registered trademark for 25-OH-D3; available from DSM Nutritional Products, Switzerland) has been used to promote bone health in poultry, swine, and for vitamin D deficiency in humans. WO2008/031602 (DSM IP ASSETS, BV) describes its use for milk fever in cows.

The combination of 25-OH D3 and canthaxanthin has also been used in poultry. WO2010/057811 (DSM IP ASSETS, BV) describes this combination for use in improving hatchability, fertility, and lower embryo mortality in poultry. The combination is commercially available under the trademark MAXICHICK. There is no mention in the patent publication of the inclusion of ascorbic acid and high vitamin E levels, nor the uses to ameliorate the adverse effects of hyperphagia-related obesity.

Vitamin C (ascorbic acid) is often not included as a supplement in poultry diets, as the chicken can under normal rearing conditions can produce sufficient Vitamin C. However, it has been used in some specific conditions, such as in heat stress situations.

Vitamin E is generally added to poultry feed. Recommended doses for poultry species tends to range from about 50-100 IU/kg feed, depending on the age of the animal.

WO14/191153 (DSM IP ASSETS B.V) teaches the combination of canthaxanthin and at least one of Vitamin C, Vitamin E, selenium, and optionally at least one of thymol, eugenol, vanillin and gamma-terpinene can improve immune statues, bone health, skeletal development and growth and feed conversion, particularly when flocks are subject to stress associated with vaccination.

WO14/202433 (DSM IP ASSETS B.V) teaches the combination of canthaxanthin and 25-OH D3 to improve internal egg quality, i.e. enhancing the strength of vitelline membrane that envelops the yolk. There is no teaching to add ascorbic acid to the combination, nor for its use in ameliorating the adverse effects of hyperphagia-related obesity.

There is a need to prevent or delay the onset of ovarian diseases in bovines, and to prolong their reproductive life.

DETAILED DESCRIPTION OF THE INVENTION

It has been found, accordance with this invention that the combination of 25-hydroxyvitamin D (25-OH D3 and/or 25-OH D2) and antioxidants/anti-inflammatories can benefit ovarian health, and particularly polycystic ovarian syndrome in poultry. Bovines, and particularly cows suffer a similar disease, cystic ovarian disease (COD) and thus one aspect of this invention is the use of 25-OH D and antioxidants/anti-inflammatories to prevent, treat, and/or ameliorate COD in bovines.

Also it has been found that the combination of 25-OH D and antioxidants/anti-inflammatories can preserve levels of 17-β estradiol, and that this preserves the reproductive life of laying hens. As 17-β estradiol is an important circulating hormone for bovine fertility as well, another aspect of this invention is the use of the combination of 25-OH D and antioxidants/anti-inflammatories to preserve levels of 17-β estradiol in bovines, particularly milking cows and those used in breeding.

It has also been found in accordance with this invention, that the bio-actives traditionally thought of as antioxidants also possess an anti-inflammatory activity which benefits ovarian health.

As 25-OH D2 and 25-OH D3 may act in a similar fashion after administration, it is envisioned that either may be used separately in combination with antioxidants/anti-inflammatories, or a mixture of both 25-OH D3 and 25-OH D2 may be used in combination with antioxidants/anti-inflammatories. If used together, the ratio of 25-OH D3:25-OH D2 is not a critical part of the invention. 25-OH D3 used alone is preferred.

The antioxidants/anti-inflammatories of this invention comprise the combination of ascorbic acid, vitamin E and a carotenoid. The carotenoid is at least one selected from the group consisting of: lycopene, astaxanthin, cryptoxanthin, beta-carotene, lutein, zeaxanthin and canthaxanthin. Most preferred are lycopene, astaxanthin, lutein, and zeaxanthin. Thus one aspect of this invention is the combination of 25-OH D3, one or more of the aforementioned carotenoids, vitamin E and ascorbic acid. Another embodiment is the combination of 25-OHD2, one or more of the aforementioned carotenoids, Vitamin E and ascorbic acid. Another embodiment is the combination of 25-OHD3, 25-OHD2, one or more of the aforementioned, Vitamin E and ascorbic acid.

Compositions

Another aspect of this invention is the combination of
a) 25-OH D,
b) a carotenoid selected from the group consisting of: lycopene, astaxanthin, cryptoxanthin, beta-carotene, lutein, zeaxanthin and canthaxanthin,
c) vitamin E,
d) ascorbic acid, and
e) optionally further comprises at least one further bio-active ingredient selected from the group consisting of:
Vitamin D, Vitamin B2, Biotin, Vitamin B6, Niacin, Zinc, Copper, Manganese, and Selenium. Preferably the 25-OH D is 25-OH D3 for addition to a bovine diet to enhance ovarian health. Preferably at least Vitamin D is a further bio-active ingredient. Sometimes the further bio-active ingredients include at least Vitamin D and Selenium. In some cases, all the further bio-active ingredients are added.

A further aspect is the combination of 25-OH D, one or more carotenoids of this invention, vitamin E and ascorbic acid which optionally further comprises at least one further bio-active ingredient selected from the group consisting of Vitamin D, Vitamin B2, Vitamin B6, Niacin, Pantothenic Acid, Folic Acid, Biotin, Zinc, Copper, Manganese, Selenium, and combinations thereof, for the addition to a bovine diet to enhance ovarian health. Preferably the 25-OH D is 25-OH D3. Sometimes, the further bio-active ingredient includes biotin. Sometimes the further bio-active ingredient includes Vitamin D and biotin. Sometimes the further bio-active ingredient includes all the aforementioned optionally bio-active ingredients.

Premixes

Another aspect of this invention are premixes for bovine feed which comprise the combination of 25-OH D, vitamin E, ascorbic acid and one or more of the aforementioned carotenoids. Preferably, the 25-OH D is 25-OH D3. The premixes and subsequent nutraceutical improves/ameliorates adverse conditions associated with the ovaries, and preferably COD. In some embodiments the premix or subsequent nutraceutical also comprises at least one further bio-active ingredient selected from the group consisting of:
Vitamin D, Vitamin B2, Vitamin B6, Niacin, Zinc, Copper, Manganese, Selenium and combinations thereof. Sometimes the further bio-active ingredients include at least Vitamin D and Selenium. In some cases, all the further bio-active ingredients are added.

Another aspect of this invention are premixes for nutraceuticals which comprise which further comprise at least one further bio-active ingredient selected from the group consisting of: Vitamin D, Vitamin B2, Vitamin B6, Niacin, Pantothenic Acid, Folic Acid, Biotin, Zinc, Copper, Manganese, Selenium and combinations thereof. Sometimes, the further bio-active ingredient includes biotin. Sometimes the further bio-active ingredient includes Vitamin D and biotin. Sometimes the further bio-active ingredient includes all the aforementioned optionally bio-active ingredients.

In another aspect, the 25-OH D and antioxidants/anti-inflammatories of this invention are all used in bovines which are fed a complete diet, so they are not vitamin/mineral deficient. Thus, the 25-OH D and antioxidant/combination of this invention is not acting to remedy a vitamin or other nutrient deficiency. It can be considered a supra-physiological dosage.

In some embodiments the 25-OH D and antioxidants/anti-inflammatories of this invention are the sole additive ingredients to a basal diet.

Figure 1:
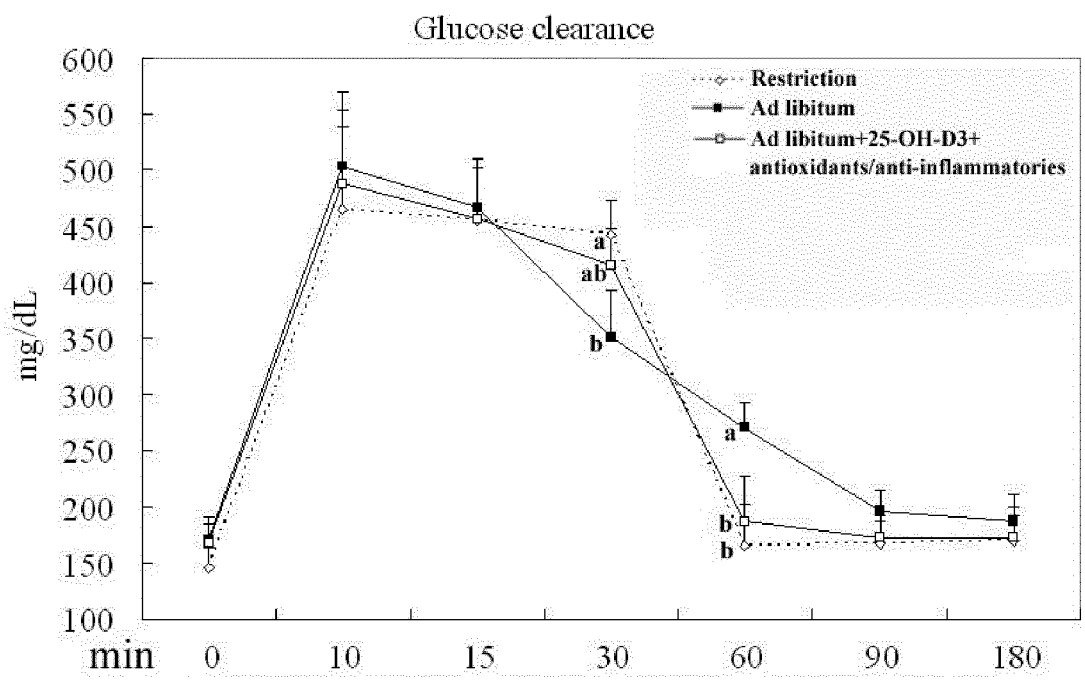
FIG. 1 shows glucose clearance and insulin secretion of broiler breeder hens in response to ad libitum feed intake in combination with 25-OH D3+antioxidants/anti-inflammatories. Hens were injected with a single dose of glucose (0.5 g/kg BW) through wing vein after 3 weeks of feeding. Blood samples were collected through cannulation of wing vein at indicated time points after glucose infusion, n=3.

As used throughout the specification and claims, the following definitions apply:

"Vitamin D" means either Vitamin D2, Vitamin D3 or a combination. Vitamin D3 used alone is preferred.

"Ascorbic Acid" and "Vitamin C" are used interchangeably throughout the specification and claims.

"Basal diet" means that the food used supplies the animal with sufficient vitamins and minerals so that the bovine is vitamin and mineral replete.

"Bovine" means cows, particularly those which are raised in the dairy industry, or for breeding purposes. It also includes other species which are used for their reproductive capability, such as buffalo, yak, or musk ox.

"25-OH-D3+antioxidants/anti-inflammatories" means the combination of 25-OH D3, vitamin E, carotenoid and ascorbic acid, administered in feed as an addition to a basal diet, at a dosage range as set forth in the specification. Optionally, and preferably, additional bio-active ingredients, selected from the group consisting of: Vitamin D, Vitamin B2, Vitamin B6, Niacin, Pantothenic Acid, Folic Acid, Biotin, Zinc, Copper, Manganese, Selenium and combinations thereof are added to the 25-OHD3, vitamin E, carotenoid and ascorbic acid combination.

"25-OH D" refers to any form of 25-hydroxyvitamin D (i.e. either 25-OH D2 or 25-OH D3, or mixes thereof). 25-OH D3 specifically refers to 25-hydroxyvitamin D3; 25-OH D2 specifically refers to 25-hydroxyvitamin D2.

"Carotenoids of this invention" means at least one of: lycopene, astaxanthin, cryptoxanthin, beta-carotene, lutein, zeaxanthin and canthaxanthin. Most preferred are at least one of: lycopene, astaxanthin, lutein, and zeaxanthin. Often, lutein and zeaxanthin are administered together.

Ovarian Problems

It has been found in accordance with this invention, that the use of a feed comprising 25-OH D3, vitamin E, one or more carotenoids of this invention and ascorbic acid can specifically contribute to ovarian health.

In hens with ovarian degeneration, large follicle atresia or tumors or other abnormal morphology such as internal ovulation, tend to have a lower egg production rate than in their past records. Hens with obesity and related dysregulations such as plasma lipids and ceramide or insulin and leptin levels, or tissue cytokine and lipid content tend to have a rapid ovarian degeneration and other abnormalities and thereby a lower egg production rate which can be easily monitored.

Polycystic ovary syndrome in humans includes symptoms such as one or more of: obesity, insulin resistance, hypertriglyceridemia, increased circulating concentrations of ceramide and non-esterified fatty acids (NEFAs), and systemic inflammogens, including IL-1β.

In cows, a similar condition to polycystic ovary syndrome is termed cystic ovarian disease (COD), and it is considered to be the most common abnormality of the ovarian function and thus infertility in dairy cattle. Cows with COD tend to have extended calving intervals and increased number of insemination per conception, and are a greater risk of being culled. COD is traditionally defined as the presence of a large follicle-like structure on one of the ovaries, having a diameter of 2.5 cm or greater, that persists for at least 10 days. The disease pathogenesis is not fully understood, but follicular cyst development appears to involve a hypothalamic unresponsiveness to estradiol. (see Hein et al 2015 *Animal Reproduction Science* 156: 64-74).

Thus, another aspect of this invention is the use of Thus, one aspect of this invention is the use of 25-OHD and antioxidants/anti-inflammatories to ameliorate COD in bovines.

Ameliorate Decrease in 17-β—Estradiol Levels

It has been found, accordance with this invention that the combination of 25-hydroxyvitamin D (25-OH D3 and/or 25-OH D2) and antioxidants/anti-inflammatories ameliorates the decrease of 17-β estradiol levels.

Thus, one aspect of this invention is the use of 25-OHD and antioxidants/anti-inflammatories to ameliorate a decrease of 17-β estradiol levels of bovines and thereby extend their productive life; preferably the bovine is a milking cows or cow kept as breeders.

17-β estradiol is the endogenous hormone in cows that induces estrous behavior. Many cows do not readily re-enter estrous after calving, or the length of estrous is not long enough to ensure insemination. The combination of 25-OH D3 and antioxidants/anti-inflammatories can thus help maintain a higher level of 17-β estradiol in cows.

3. Doses

In one aspect of this invention the combination of 25-OH D3 and the antioxidants/anti-inflammatories of this invention are administered to vitamin replete rather than vitamin deficient individuals. The vitamin replete status is preferably due to the a balanced diet which supplies at least the minimum amount of vitamins and minerals for the person. The combination of this invention is thus preferably used in addition to the basic diet.

25-OH D3:25-OH D3 is present in a daily dosage is from 2500 IU to 40000 IU, preferably about 25000 IU and 30000 IU.

Vitamin E: The amount in a daily dosage can range from 500-4000 mg/day, preferably from 1000-4000 mg/day.

Ascorbic Acid: The amount of ascorbic acid can range from 250-500 mg/day.

Lycopene: The amount of lycopene can range from 15-1250 mg/day; preferably 500-800 mg/day.

Astaxanthin: The amount of astaxanthin can range from 1-150 mg/day, preferably 2-50 mg/day, more preferably 5-20 mg/day.

β-cryptoxanthin The amount of β-cryptoxanthin can range from 1-100 mg/day; preferably from 2-30 mg/day; and more preferably from 5-15 mg/day.

Beta-carotene The amount of beta-carotene can range from 300-1000 mg/day; preferably from 500-800 mg/day.

Zeaxanthin: The amount of zeaxanthin can range from 1-60 mg/day; preferably 2-20 mg/day; and more preferably 3-10 mg/day.

Lutein: The amount of lutein can range from 1 to 200 g/day, preferably from 50 mg/day.

Canthaxanthin: The amount of canthaxanthin should not exceed 20 mg/day.

Representative Daily Formula 1:
25-OH D3: 2500-40000 IU, preferably 25000 IU
Vitamin E 4000 mg
Ascorbic acid: 250-500 mg, preferably 500
Cryptoxanthin: 10 mg
Representative Daily Formula #2:
25-OH D3: 2500-40000 IU, preferably 30000 IU
Vitamin E: 1000 mg
Ascorbic acid: 250-500 mg, preferably 500
Lutein 500-800 mg
(optional) Zeaxanthin: 6 mg
Representative Daily Formula #3
25-OH D3: 2500-40000 IU, preferably 30000 IU
Vitamin E: 1000-3000 mg
Ascorbic acid: 250-500 mg
Lycopene: 20 mg
Representative Daily Formula #4
25-OH D3: 2500-40000 IU, preferably 25000 IU
Vitamin E: 200-600 mg, preferably 300-500 mg
Ascorbic acid: 250-500 mg, preferably 500
Astaxanthin: 20 mg Representative Daily Formula #5
25-OH D3: 2500-40000 IU, preferably 30000 IU
Vitamin E: 200-600 mg, preferably 300-500 mg
Ascorbic acid: 250-500 mg, preferably 500
Beta Carotene: 500-800 mg
Preferred ratios include the following

| Vit E | Vit C | Carotenoid |
|-------|-------|------------|
| 1-10  | 1-10  | 1          |
| 1-20  | 1-10  | 1          |
| 1-20  | 1-20  | 1          |
| 1-10  | 1-20  | 1          |

Optional Additional Ingredients

To each of the nutraceutical, food supplement or pharmaceutical composition listed above, at least one of the additional ingredients may be added. Preferably at least one, and more preferably more than one of the following ingredients are added. In other embodiments, all the following ingredients are added:

Vitamin D3—The amount of vitamin D3 can range from 1-100 µg/day; preferably from 1-50 µg/day and more preferably 5-25 µg/day.

Vitamin B2: The amount of Vitamin B2 can range from 0.5-300 mg/day; preferably from 5-100 mg/day and more preferably 10-50 mg/day.

Niacin: The amount of Niacin can range from 1-300 mg/day; preferably from 5-100 mg/day and more preferably 10-50 mg/day.

Pantothenic acid: The amount of Pantothenic acid can range from 1-300 mg/day; preferably from 5-100 mg/day and more preferably 10-50 mg/day.

Folic acid: The amount of Folic acid can range from 50-100 µg/day; preferably from 400-800 µg/day and more preferably 400-600 µg/day.

Biotin: The amount of Biotin can range from 5 µg to 10 mg/day; preferably from 30 µg to-5 mg/day and more preferably 0.1-1 mg/day.

Zinc: The amount of Zinc can range from 1-40 mg/day; preferably from 5-40 mg/day and more preferably 10-20 mg/day.

Copper: The amount of Copper can range from 0.4-10 mg/day; preferably from 0.7-5 mg/day and more preferably 0.9-3 mg/day.

Manganese: The amount of Manganese can range from 1-10 mg/day; preferably from 1-5 mg/day and more preferably 1-3 mg/day.

Selenium: The amount of Selenium can range from 20-400 µg/day; preferably from 50-200 µg/day and more preferably 50-100 µg/day.

Premixes can be made to give the above-mentioned doses and preferred doses. One premix which forms part of this invention is formulated so that 1 gram of premix is added to one kilogram nutraceutical, food supplement or pharmaceutical composition, and that the resulting nutraceutical, food supplement or pharmaceutical composition contains the dosages described in any of the given dosages above. The amounts of the individual ingredients can, of course be varied so that one kilogram of premix is added to one metric ton of nutraceutical, food supplement or pharmaceutical composition and that the resulting feed contains the dosages described in any of the given dosages above. There are specific illustrations of this in the Examples, below.

The following non-limiting Examples are presented to better illustrate the invention.

EXAMPLES

Example 1

A total of thirty 45-week-old broiler breeder hens (ROSS 308) were obtained from a commercial flock for the study. A basal broiler breeder laying diet was formulated as shown in Table 1. The calculated nutrient composition is shown in Table 2.

TABLE 1

Ingredient composition of the basal broiler breeder laying diets.

| Composition | %, w/w |
|-------------|--------|
| Corn | 66.9 |
| Soybean meal | 22.2 |
| Oil fat | 1.67 |
| Ca Carbonate (ground oyster shell) | 6.36 |
| Dicalcium phosphate | 1.8 |
| Choline-Cl (70%) | 0.1 |
| Mineral Premix[1] | 0.1 |
| Copper sulfate | 0.05 |
| Vitamin Premix[2] | 0.1 |

[1]Mineral premix provided (per kg of diet for treatment groups 1, 2 and 3): Cu 18 mg; Iodine 1.1 mg; Fe 80 mg; Mn 150 mg; Zn 125 mg; and Se 0.25 mg.
[2]Refer to Table 2 for further detail.

TABLE 2

Vitamin premix composition (provided per kg of diet)

| Vitamin | Treatments 1 and 2<br>1 = restricted feeding<br>2 = ad libitum feeding | Treatment 3<br>3 = ad libitum feeding +<br>25-OH-D3 +<br>antioxidants/anti-<br>inflammatories |
|---------|----|----|
| A (IU) | 10000 | 12000 |
| D3 (IU) | 2500 | 3000 |
| E (mg) | 100 | 150 |
| K3 (mg) | 3 | 5 |
| B1 (mg) | 3 | 5 |
| B2 (mg) | 8 | 14 |
| B6 (mg) | 6 | 8 |
| B12 (mg) | 0.03 | 0.03 |
| Niacin (mg) | 60 | 120 |
| Pantothenic acid (mg) | 18 | 30 |
| Folic acid (mg) | 1 | 4 |
| Biotin (mg) | 0.2 | 0.4 |
| C (ascorbic acid) (mg) | 0 | 150 |
| 25-OH-D3 (mcg) | 0 | 69 |
| Canthaxanthin (mg) | 0 | 6 |

TABLE 3

Calculated nutrient composition (%) of the basal broiler breeder laying diets.

| Composition | % w/w |
|-------------|-------|
| Crude protein | 16 |
| Crude fat | 4.2 |
| Calcium | 3.1 |
| Sodium | 0.16 |
| Total Phosphorus | 0.64 |
| Total ME | 2910 kcal/kg |

Diet was supplemented with or without 25-OH D3 at 69 mcg/kg diet in combination with antioxidants/anti-inflammatories (vitamin E, ascorbic acid, canthaxanthin) and enriched levels of selected vitamins. Hens were randomly allocated to 3 treatment groups according to feeding regimen (restricted and ad libitum) as follows:
Basal diet—restricted feeding (140 g/day)
Basal diet—ad libitum feeding
Basal diet—ad libitum feeding+25-OH-D3 at 69 mcg/kg diet+antioxidants/anti-inflammatories They were individually-housed in wire cages placed in a controlled room with 14 h:10 h light:dark period and at a temperature of 25±3° C. Water was available ad libitum. The experimental period was lasted for 10 weeks. Three weeks after the feeding trial, some birds were used for relevant plasma parameter analyses. At the end of experiment, hens were euthanized and sacrificed for tissue sample collection for further studies:

Example 2

Results and Discussion

25-Hydroxy D3 and Antioxidants/Anti-Inflammatories Lowered Mortality and Improved Egg Production, Ovarian Morphology and Plasma 176 Estradiol Level Secretion of estradiol is the hallmark of successful ovulatory follicles. In addition to its role in triggering the preovulatory surge of gonadotropins, estradiol is an important intra-ovarian growth, differentiation, and survival factor. Inclusion of 25-hydroxy D3 and antioxidants/anti-inflammatories reduced mortality and incidence of ovarian degeneration and ovarian-tumor-like morphology, increased egg production and sustained plasma estradiol levels in birds under ad libitum feed intake.

25-OH D3 and Antioxidants/Anti-Inflammatories Ameliorated Impaired Glucose Clearance and Insulin Sensitivity Dietary inclusion of 25-OH D3 and antioxidants/anti-inflammatories improves insulin resistance as evidenced by ameliorating fasting plasma glucose and non-esterified fatty acid level in overfed hens for 10 weeks (TABLE 4). In glucose clearance test, lean hens showed a very sharp clearance rate between 30-60 min after glucose infusion, and conversely obese hens had a very sluggish clearance rate between 30-90 min (FIG. 1). In insulin secretion, obese hens showed a higher plasma insulin level under fasting status and after glucose infusion when compared to lean hens (FIG. 1). Both glucose clearance and glucose-induced insulin secretion were corrected by 25-OH D3 and antioxidants/anti-inflammatories inclusion in overfed hens for 3 weeks (FIG. 1).

TABLE 4

25-OH D3 and antioxidants/anti-inflammatories on plasma glucose, non-esterified fatty acid (NEFA) and insulin of ad libitum-fed broiler breeder hens

|  | Restricted feeding | Ad libitum feeding | Ad libitum feeding + 25-OH-D3 + + antioxidants/anti-inflammatories | Pooled SEM[1] |
|---|---|---|---|---|
| After 3 weeks of feeding |  |  |  |  |
| Plasma glucose (mg/dL) | 181.5 | 202.5 | 188.5 | 11.9 |
| Plasma NEFA (μmole/mL) | 0.21[b] | 0.35[a] | 0.25[b] | 0.05 |
| After 10 weeks of feeding |  |  |  |  |
| Plasma glucose (mg/dL) | 180.6[b] | 212.6[a] | 195.6[b] | 12.7 |
| Plasma NEFA (μmole/mL) | 0.35[b] | 0.44[a] | 0.33[b] | 0.05 |
| Fasting plasma insulin | 1.38 | 1.15 | 1.59 | 0.21 |
| Glucose-induced insulin | 2.66a | 1.97b | 2.46a | 0.36 |

[a-b]Within a row, means without a common superscript differ ($P < 0.05$).

[1]Pooled standard error of the mean.

25-OH D3 and Antioxidants/Anti-Inflammatories Ameliorated Dyslipidemia

Ad libitum-fed hens elevated plasma triglyceride, ceramide and sphingomyelin levels. However, supplementation of combined 25-OH D3 and antioxidants/anti-inflammatories lowered the level of these lipid metabolites in the plasma of ad libitum-fed hens (TABLE 5).

TABLE 5

25-OH D3 and antioxidants/anti-inflammatories on plasma triacyglycerol, ceramide and sphingomyelin of ad libitum-fed broiler breeder hens

|  | Restricted feeding | Ad libitum feeding | Ad libitum feeding + 25-OH-D3 + + antioxidants/anti-inflammatories | Pooled SEM[1] |
|---|---|---|---|---|
| After 3 weeks of feeding |  |  |  |  |
| Plasma triacyglycerol (mg/mL) | 15.6 | 17.4 | 14.5 | 2.9 |
| Plasma ceramide (nmole/mL) | 11.5[b] | 18.2[a] | 13.5[b] | 2.83 |
| Plasma sphingomyelin (μmole/mL) | 0.14[b] | 0.28[a] | 0.16[b] | 0.05 |
| After 10 weeks of feeding |  |  |  |  |
| Plasma triacyglycerol (mg/mL) | 12.75[b] | 15.2[a] | 11.5[b] | 2.2 |
| Plasma ceramide (nmole/mL) | 8.1[b] | 12.3[a] | 8.8b | 1.65 |
| Plasma sphingomyelin (μmole/mL) | 0.15[b] | 0.22[a] | 0.12[b] | 0.05 |

[a-b]Within a row, means without a common superscript differ ($P < 0.05$).

[1]Pooled standard error of the mean.

25-OH D3 and Antioxidants/Anti-Inflammatories Reduced Accumulation of Tissue Triglyceride and Ceramide Content Accumulation of triglyceride and ceramide in the liver, heart and leg muscles was lower in hens fed supplemental 25-OH D3 and antioxidants/anti-inflammatories than in those fed ad libitum (Table 6).

TABLE 6

25-OH D3 and antioxidants/anti-inflammatories on tissue triacyglycerol and ceramide content of ad libitum-fed broiler breeder hens

|  | Restricted feeding | Ad libitum feeding | Ad libitum feeding + 25-OH-D3 + Antioxidants + anti-inflammatories | Pooled SEM[1] |
|---|---|---|---|---|
| Triacyglycerol (mg/g tissue) | | | | |
| Liver | 69.0$^b$ | 94.8$^a$ | 79.8$^a$ | 10.6 |
| Heart | 33.1$^b$ | 55.6$^a$ | 45.6$^a$ | 6.8 |
| Breast muscle | 15.6 | 18.0 | 17.4 | 0.05 |
| Leg muscle | 30.2$^c$ | 52.3$^a$ | 41.2$^b$ | 6.6 |
| Ceramide (mg/g tissue) | | | | |
| Liver | 174.5$^b$ | 287.9$^a$ | 235.0$^a$ | 52.7 |
| Heart | 17.5$^c$ | 30.2$^a$ | 23.5$^b$ | 2.4 |
| Breast muscle | 2.25 | 2.91 | 2.52 | 0.54 |
| Leg muscle | 4.12$^b$ | 7.12$^a$ | 6.01$^a$ | 0.85 |

$^{a\text{-}b}$Within a row, means without a common superscript differ (P < 0.05).
[1]Pooled standard error of the mean.

Figure 2:
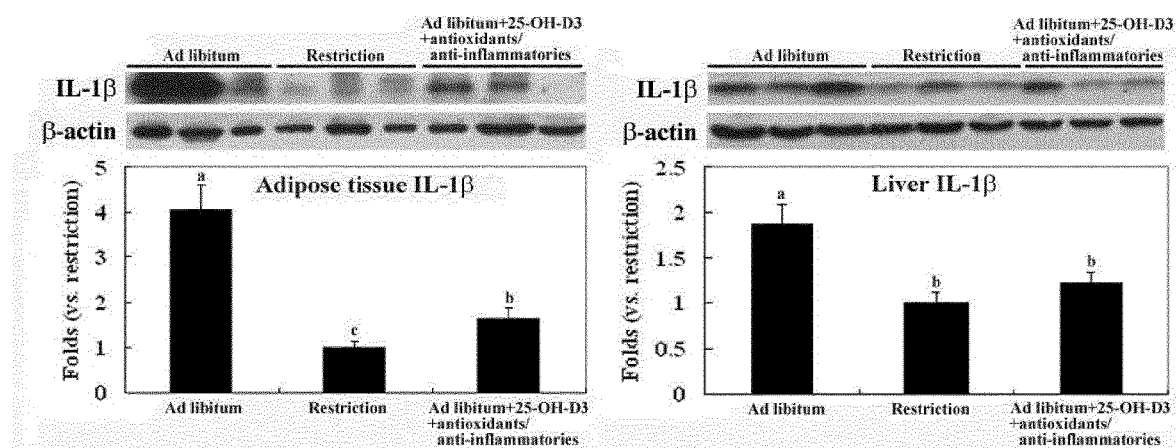
FIG. 2 shows tissue interleukin-1β contents and plasma IL-6 levels of broiler breeder hens in response to ad libitum feed intake in combination with 25-OH D3 and antioxidants/anti-inflammatories. Tissues and blood samples were collected after 10 weeks of the feeding trial. Means with different superscript letters are significantly different (P<0.05), n=3.
Figure 3:
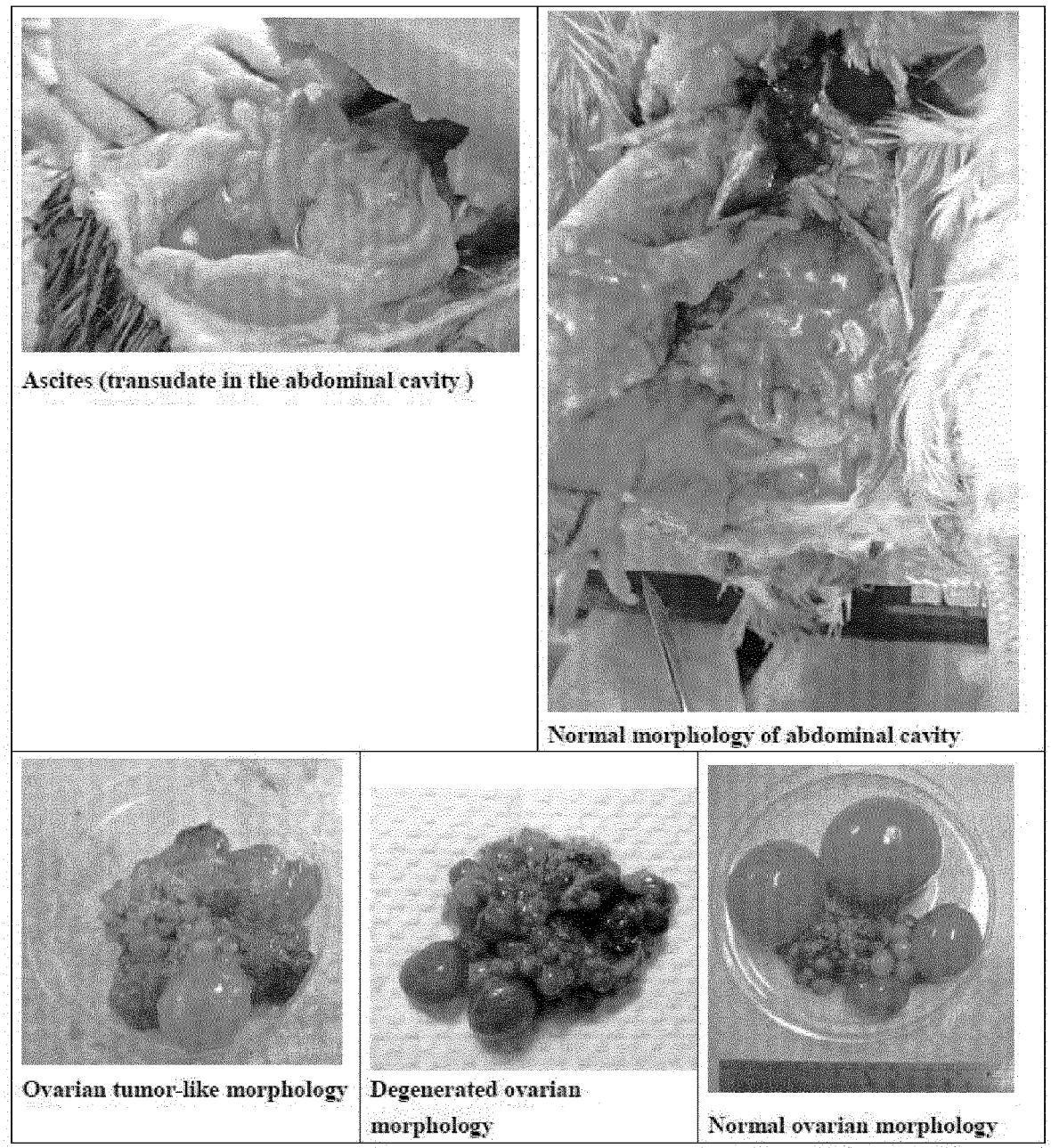
FIG. 3 shows photographs of ascites seen in poultry abdomen and ovarian malformations in poultry.

25-OH D3 and Antioxidants/Anti-Inflammatories Depressed Tissue Proinflammatory IL-1β Production and Plasma IL-6 Concentrations in Overfed Broiler Hens Obesity-associated inflammation was ameliorated by dietary 25-OH D3 and antioxidants/anti-inflammatories supplementation as evidenced by suppressed circulating IL-6 levels and IL-1β production in adipose tissue, liver, leg and breast muscle, and heart (FIG. 2).

25-OH D3 and Antioxidants/Anti-Inflammatories Ameliorated Lipotoxicity in Broiler Breeder Hens Fed Ad Libitum A central complication of obesity is the development of insulin resistance, which is when insulin is incapable of eliciting postprandial nutrient storage in its primary target tissues, skeletal muscle and liver. Without wishing to be bound by theory, it appears that two probable mechanisms may explain how increased adipose stores affect overall insulin sensitivity throughout the body, contributing to the down regulation of insulin signaling in peripheral tissues. Firstly, the delivery of nutrients to cells or tissues is in excess of their storage capacities and thus this leads to the generation of metabolites that inhibit insulin action. Of particular importance, lipid derivatives, such as triacylglycerol and ceramide, have been shown to inhibit specific insulin signaling intermediates, thus blocking postprandial glucose uptake and/or glycogen synthesis. In the case of broiler breeder females being fed ad libitum, the persistent accumulation of these metabolites in peripheral tissues likely contributes to a sustained state of insulin resistance throughout the hen and of lipotoxic development. Secondly, increased adiposity induces a chronic inflammatory state characterized by elevated circulating levels of proinflammatory cytokines produced from adipocytes or from macrophages infiltrating the fat pad. These inflammatory mediators have been shown to antagonize insulin signaling directly, and also to induce catabolic processes, thus further increasing the delivery of nutrient metabolites to insulin-responsive organs.

Overall, excess supply of glucose leading to the formation of excess saturated fatty acids and therefore accumulation of lipids in non-adipose tissues elevates the cellular levels of—active lipids (sphingolipids) that inhibit the signaling pathways implicated in metabolic regulation together with activated inflammatory responses and lipotoxic development. In particular, ceramide is a putative intermediate linking both excess nutrients (i.e., saturated fatty acids) and inflammatory cytokines to the induction of insulin resistance. Moreover, ceramide is toxic in a variety of different cell types and is capable of damaging the heart, pancreas and vasculature. Moreover, 25-hydroxy D3 and antioxidants/anti-inflammatories were effective in ameliorating the deleterious effect of metabolic and endocrine dysregulations and pro-inflammatory responses resulting from increased adiposity occurring in broiler breeder hens fed to satiation.

25-OH D3 and Antioxidants/Anti-Inflammatories Ameliorate Cardiac Morbidities, Ascites, and Inflammation in Overfed Broiler Hens The heart may become dysfunctional due to excess lipid accumulation. That ad libitum feeding promoted triglyceride accumulation in the heart suggested that increased cardiac fatty acid availability is adaptively esterified into triglyceride. In addition, ceramide content of the heart was also increased as a result of ad libitum feeding. Ceramide is a cardiotoxin in lipotoxic cardiomyopathy, which elicited inflammatory responses as evidenced by more cardiac infiltration of immune cells. (Table 7).

TABLE 7

25-OH D3 and antioxidants/anti-inflammatories on cardiac responses of ad libitum-fed broiler breeder hens

|  | Restricted feeding | Ad libitum feeding | Ad libitum feeding + 25-OH-D3 + antioxidants + anti-inflammatories | Pooled SEM[1] |
|---|---|---|---|---|
| Heart weight (g) | 14.5$^b$ | 19.2$^a$ | 17.3$^a$ | 1.8 |
| Heart/body weight (%) | 0.40 | 0.47 | 0.43 | 0.17 |
| Heart septum (HS) weight (g) | 2.73 | 3.01 | 2.83 | 0.57 |
| HS weight/heart weight (%) | 18.7 | 14.6 | 15.7 | 3.9 |
| Right atrium (RA) wall weight (g) | 1.20$^b$ | 1.97$^a$ | 1.72$^{ab}$ | 0.38 |
| RA wall weight/heart weight (%) | 8.2 | 9.6 | 9.6 | 1.9 |
| Right ventricle (RV) wall weight (g) | 0.95$^b$ | 1.51$^a$ | 1.73$^a$ | 0.27 |
| RV wall weight/heart weight (%) | 6.3$^b$ | 7.5$^{ab}$ | 9.4$^a$ | 1.5 |
| Left atrium (LA) wall weight (g) | 1.17$^b$ | 2.26$^a$ | 2.02$^a$ | 0.43 |
| LA wall weight/heart weight (%) | 12.2 | 11.1 | 10.9 | 3.1 |

TABLE 7-continued

25-OH D3 and antioxidants/anti-inflammatories on cardiac responses of ad libitum-fed broiler breeder hens

| | Restricted feeding | Ad libitum feeding | Ad libitum feeding + 25-OH-D3 + antioxidants + anti-inflammatories | Pooled SEM[1] |
|---|---|---|---|---|
| Left ventricle (LV) wall weight (g) | 3.78[b] | 4.45[a] | 4.65[a] | 0.34 |
| LV wall weight/heart weight (%) | 25.5[a] | 21.7[b] | 25.8[ab] | 2.4 |
| Incidence of transudate within pericardium (heart/total) | 1/7 | 5/10 | 3/10 | |
| Incidence of heart ventricle dilation (heart/total) | 1/7 | 6/10 | 3/10 | |
| Incidence of ascites (hen/total) | 0/7 | 3/10 | 1/10 | |
| Cardiac immune cell count | 97.9[a] | 127.7[a] | 57.7[b] | 32.4 |

[a-b]Within a row, means without a common superscript differ ($P < 0.05$).
[1]Pooled standard error of the mean.

Cardiac hypertrophy represents clinically an adaptive response to increased workload on the heart. However, cardiac responses to neural and hormonal factors can also incite hypertrophic changes independent of increases in afterload or vascular resistance. Fuel overloading-induced cardiac compensatory growth occurred in broiler breeder hens. Cardiac hypertrophy may become maladaptive and eventually develop into pathological conditions, leading to heart failure. These results supported the fact that lipotoxic development and hypertrophic growth in the heart tend to elicit inflammatory responses.

Figure 4:
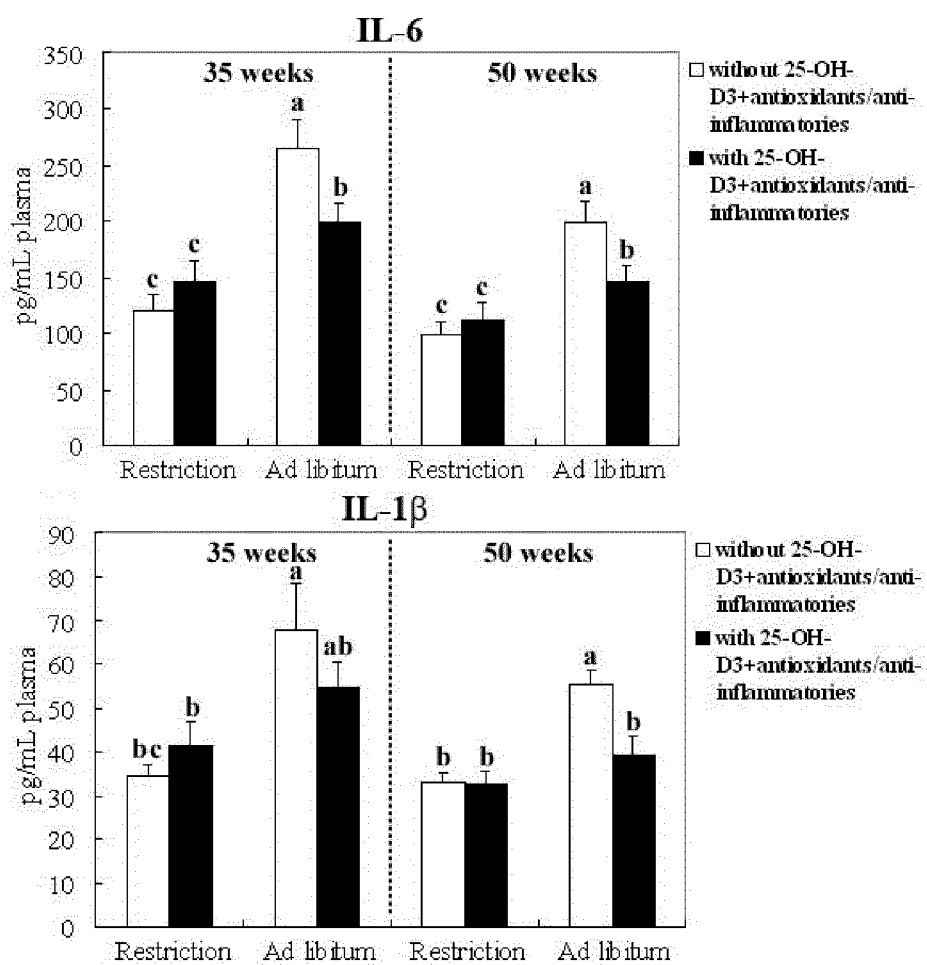
FIG. 4 are graphs showing the effect of dietary supplementation of 25-OH-D3+antioxidants/anti-inflammatories on plasma IL-6 and IL-1β concentration of broiler hens with restricted or ad libitum feed intake.

FIG. 4 shows the effect of dietary supplementation of 25-OH-D3+antioxidants/anti-inflammatories on plasma IL-6 (top graphs) and IL-1β concentration (lower graphs) of broiler hens with restricted or ad libitum feed intake. Results were expressed with mean±SEM (n=6). Means with different letters over the bars are significantly different (P<0.05) Conclusions and Annotations from FIG. 4:

25-OH-D3+antioxidants/anti-inflammatories ameliorated chronic systemic inflammation in hens fed ad libitum.

The invention claimed is:

1. A method of treating or delaying the onset of or ameliorating a symptom of bovine cystic ovary disease or enhancing bovine ovarian health by administering a composition comprising 25000-30000 IU 25-Hydroxy vitamin D (25-OH D), 250-500 mg Vitamin C, 1000-4000 mg Vitamin E, and one or more carotenoids selected from the group consisting of: lycopene, astaxanthin, cryptoxanthin, beta-carotene, lutein, zeaxanthin and canthaxanthin per day to a vitamin replete bovine.

2. The method according to claim 1, wherein the composition further comprises at least one further bio-active ingredient selected from the group consisting of: Vitamin D, Vitamin B2, Vitamin B6, Niacin, Pantothenic Acid, Folic Acid, Biotin, Zinc, Copper, Manganese, and Selenium.

3. The method according to claim 1, wherein the 25-hydroxy vitamin D is 25-hydroxy vitamin D3 (25-OH D3).

\* \* \* \* \*